(12) United States Patent
Stapleton

(10) Patent No.: US 11,679,241 B2
(45) Date of Patent: Jun. 20, 2023

(54) BALLOON CATHETER WITH ADJUSTABLE INNER MEMBER

(71) Applicant: CLEARSTREAM TECHNOLOGIES LIMITED, Enniscorthy (IE)

(72) Inventor: Corey E. Stapleton, Gilbert, AZ (US)

(73) Assignee: CLEARSTREAM TECHNOLOGIES LIMITED, Enniscorthy (IE)

( * ) Notice: Subject to any disclaimer, the term of this patent is extended or adjusted under 35 U.S.C. 154(b) by 650 days.

(21) Appl. No.: 16/682,273

(22) Filed: Nov. 13, 2019

(65) Prior Publication Data

US 2020/0094029 A1    Mar. 26, 2020

Related U.S. Application Data

(63) Continuation of application No. 14/758,622, filed as application No. PCT/US2013/078427 on Dec. 31, 2013, now Pat. No. 10,518,068.

(60) Provisional application No. 61/747,448, filed on Dec. 31, 2012.

(51) Int. Cl.
*A61M 25/10*  (2013.01)
*A61M 25/00*  (2006.01)

(52) U.S. Cl.
CPC .... *A61M 25/1025* (2013.01); *A61M 25/0097* (2013.01); *A61M 25/104* (2013.01); *A61M 2025/1068* (2013.01); *A61M 2025/1093* (2013.01)

(58) Field of Classification Search
CPC .......... A61M 25/1025; A61M 25/0097; A61M 25/104; A61M 2025/1068; A61M 2025/1093
See application file for complete search history.

(56) References Cited

U.S. PATENT DOCUMENTS

| | | | |
|---|---|---|---|
| 4,276,874 A | 7/1981 | Wolvek et al. | |
| 5,423,755 A | 6/1995 | Kesten et al. | |
| 5,484,409 A | 1/1996 | Atkinson et al. | |
| 5,968,012 A * | 10/1999 | Ren | A61M 25/104 |
| | | | 604/103 |
| 6,743,210 B2 | 6/2004 | Hart et al. | |
| 2009/0177236 A1 | 7/2009 | Saab et al. | |
| 2015/0367108 A1 | 12/2015 | Stapleton | |

FOREIGN PATENT DOCUMENTS

WO    2007094374 A1    8/2007
WO    2014106226 A2    7/2014

OTHER PUBLICATIONS

English Translation of WO200709437A1 dated Aug. 23, 2007.

* cited by examiner

*Primary Examiner* — Thomas McEvoy
(74) *Attorney, Agent, or Firm* — Dickinson Wright PLLC; Andrew D. Dorisio

(57) ABSTRACT

A balloon catheter (10) with a shaft (14,24) extending in a longitudinal direction and having a proximal end and a distal end and an inflatable balloon positioned along the shaft. The balloon (12) includes at least one portion connected to the shaft and adapted for moving toward the proximal end thereof when the balloon is inflated. Related aspects are disclosed.

14 Claims, 10 Drawing Sheets

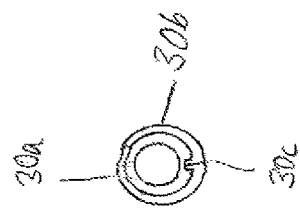
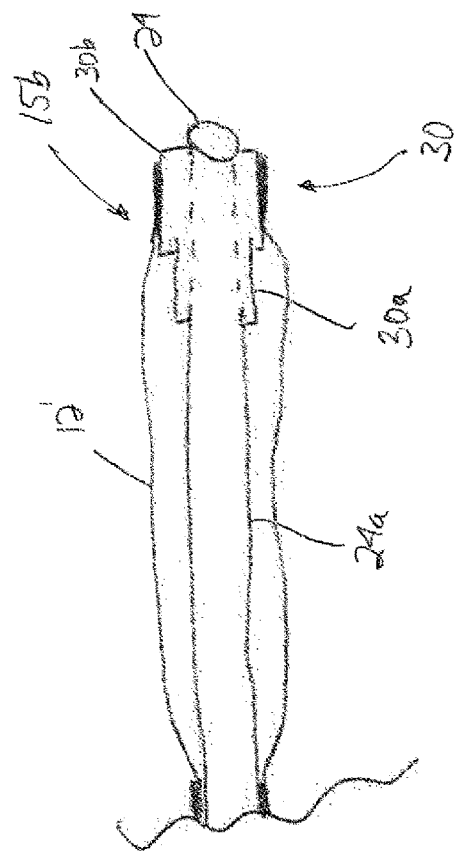
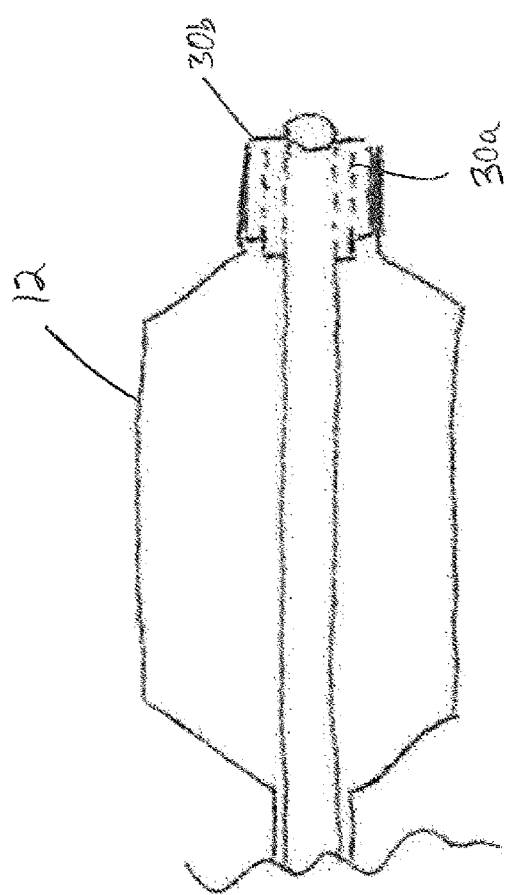

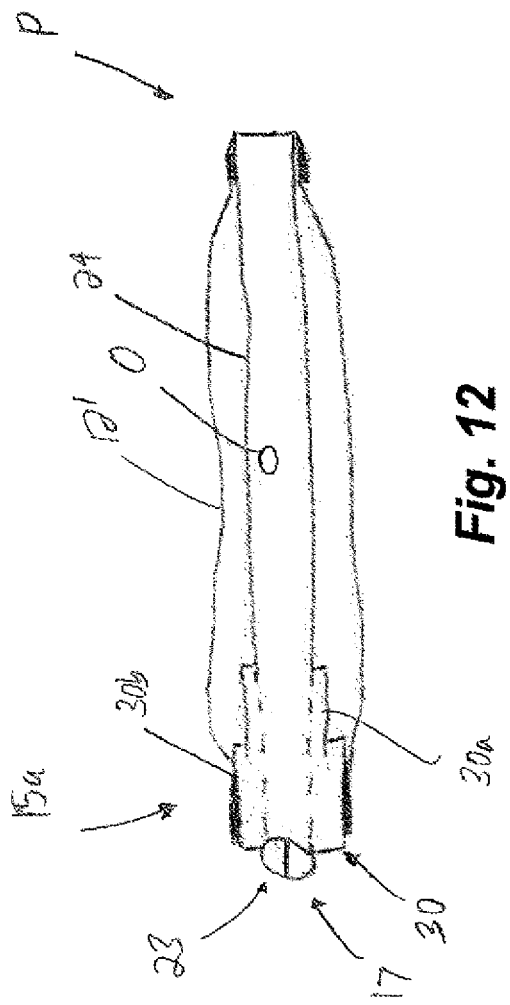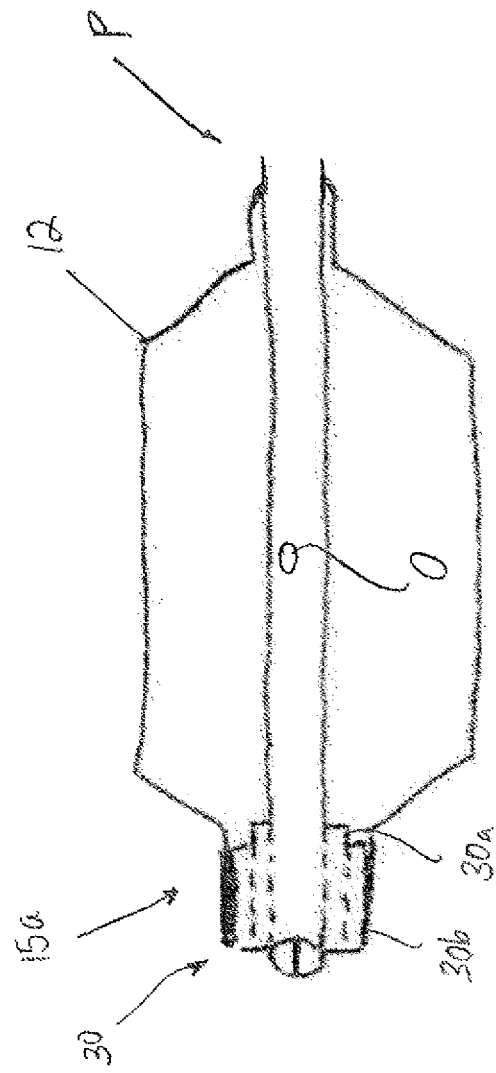

BALLOON CATHETER WITH ADJUSTABLE INNER MEMBER

This application is a continuation of U.S. application Ser. No. 14/758,622, which is a national stage of PCT/US2013/078427, which claims priority to U.S. Provisional Application No. 61/747,448, all of which are incorporated by reference.

TECHNICAL FIELD

This disclosure relates generally to balloons for performing medical procedures, such as angioplasty and, more particularly, to a balloon catheter with an adjustable inner member.

BACKGROUND OF THE INVENTION

Balloons are routinely used to resolve or address flow restrictions or perhaps even complete blockages in tubular areas of the body, such as arteries or veins. In many clinical situations, the restrictions are caused by hard solids, such as calcified plaque, and require the use of high pressures to compact such blockages. Commercially available balloons employ complex technology to achieve high pressure requirements without sacrificing the profile of the balloon. Besides high pressure requirements, the balloons should also be resistant to puncture, easy to track and push, and present a low profile, especially when used for angioplasty.

In clinical practice, angioplasty balloons are expanded from a deflated, folded state to an expanded state within a vessel to treat a target area, such as a portion of the circumferential inner wall I of a blood vessel V, as shown in FIGS. 1 and 2. The inflation is traditionally completed using an X-ray contrast agent to provide better visibility under X-ray or other form of radiography during the interventional procedure, as illustrated in FIGS. 3 and 4 (note contrast media CM having a width DX within the wall 28 of balloon 12, which is bombarded with radiation R). Typically, a 70/30 percent mixture of contrast agent and saline is used to inflate the balloon during an angioplasty procedure.

The physician performing the angioplasty procedure should be able to locate the position of the uninflated balloon with accuracy, so that the balloon will be properly positioned once inflated. This is conventionally accomplished by attaching marker bands on the catheter Shaft in the region corresponding to the balloon working surface. This "working surface" is the surface along the portion of the balloon that is used to achieve the desired treatment effect, such as contacting the calcified plaque (which surface in the case of a balloon having conical or tapering sections at the proximal and distal ends is typically co-extensive with a generally cylindrical barrel section).

Misalignment of the marker bands during placement along the shaft sometimes results in their failure to correspond precisely to the extent of the working surface, as is shown in FIG. 5 (note misalignment amount X between each interior marker band. M carried by shaft S and working surface W of balloon 12, which also typically includes a radiopaque tip P at the distal end). Even upon exercising great care to position the markers properly on the underlying shaft in alignment with anticipated boundaries of the working surface when the balloon is inflated, there remains a tendency for mismatch due to several possible factors. One such factor may be the tolerance stack-ups arising as a consequence of the affixation of the balloon to the distal end of the catheter shaft. The balloon also has a tendency to grow in the longitudinal direction when inflated, especially with large and particularly long balloons. Another factor is the tendency of the portion of the catheter shaft within the balloon to bend or flex during inflation. This may lead to misalignment between radiopaque markers fixed to the shaft and the working surface.

Whatever the cause, the resulting misalignment may prevent the clinician from accurately identifying the location of the working surface of the balloon during an interventional procedure. This may lead to a geographic misplacement, or "miss," of the intended contact between the target area T and the working surface W of the balloon 12 (see FIG. 2). It is especially desirable to avoid such an outcome when the balloon is designed to deliver a payload (such as a drug, stent, or both) or a working element to a specified location within the vasculature, since a miss may prolong the procedure (such as, for example, by requiring redeployment of the balloon 12 or the use of another balloon catheter in the case of a drug coated balloon).

During inflation and deflation of the balloon, it is desirable to avoid certain outcomes. On inflation, the application of pressure to the balloon via the contrast agent may cause the balloon to lengthen in a differential manner and thus take on a curved, banana-like shape. This curvature can lead to misalignment of the working surface of the balloon with reference points, such as radiopaque markings provided on an underlying catheter shaft, or the targeted treatment area. This may lead to a geographic misplacement, or "miss," of the intended contact between the target area and the working surface of the balloon. It is especially desirable to avoid such an outcome when the balloon is designed to deliver a payload (such as a drug, stent, or both) or a working element to a specified location within the vasculature, since a miss may prolong the procedure (such as, for example, by requiring redeployment of the balloon 12 or the use of another balloon catheter in the case of a drug coated balloon).

Upon deflation, the balloon may also be subject to a phenomenon known as "pancaking." In this condition, the balloon 12 folds down upon itself to a flattened state. This situation may cause the balloon to be viewed through fluoroscopy as perhaps still being in the inflated condition, since the full width of the balloon may still be perceived. This can give the clinician the false perception that the balloon remains inflated, when in fact it is not.

Accordingly, the need is identified for a balloon catheter that helps to avoid the foregoing problems associated with excessive curvature on inflation, pancaking on deflation, and others

SUMMARY OF THE INVENTION

An object of the disclosure is to provide a balloon having an adjustable inner member that may allow the balloon to foreshorten on inflation.

In one aspect, a balloon catheter comprises a shaft extending in a longitudinal direction and having a proximal end and a distal end and an inflatable balloon positioned along the shaft. The balloon having at least one portion connected to the shaft and adapted for moving toward the proximal end thereof when the balloon is inflated.

In one embodiment, an actuator connects the shaft to the balloon. The actuator may comprise a first position closer to the distal end of the shaft corresponding to a deflated state of the balloon and a second position closed to the proximal end of the shaft corresponding to the inflated state of the balloon. The actuator may comprise a telescoping member including a first portion attached to the balloon and a second portion attached to the shaft. The first and second portion may include a projection and the other portion may include a recess for receiving the projection.

The actuator may further comprise a spring. The spring is preferably arranged so as to shorten the shaft when the balloon is inflated. The actuator may include threads for manually adjusting the relative position of the at least one portion of the balloon.

The portion of the balloon connected to the shaft may be a distal end portion of the balloon. A proximal end portion of the balloon may be adapted for moving toward the distal end of the shaft when the balloon is inflated.

In any embodiment, the catheter may include a hub connected to the shaft in a manner that permits relative movement between the hub and the shaft in a longitudinal direction. The hub may be connected to the shaft by a spring. The hub may be connected to the shaft by a threaded engagement.

The shaft may constrict and shortens in a longitudinal direction on inflation of the balloon. The shaft may include at least one compression spring.

Another aspect is a balloon catheter comprising a shaft that constricts in a longitudinal direction on inflation of the balloon.

Still another aspect is a medical balloon connected to a telescoping device. One end of the balloon may be connected to a shaft and the other end connected to a first portion of the telescoping device for receiving a second portion of the telescoping device.

A further aspect of the disclosure relates to a catheter shaft including a telescoping device adapted for being connected to one end of an inflatable balloon. The end may comprise a distal end or a proximal end of the balloon. The device may include a spring, the spring preferably being arranged so as to shorten the shaft when the balloon is inflated. The device may include a threaded connection between a first part and a second part adapted to telescope within the first part.

A hub may be connected to the shaft in a manner that permits relative movement between the hub and the shaft in a longitudinal direction. The hub may be connected to the shaft by a spring, the spring preferably being arranged so as to shorten the shaft when the balloon is inflated. The hub may be connected to the shaft by a threaded engagement.

The arrangement may include an inflatable balloon carried by the shaft. The arrangement may further include a compression spring for connecting a first portion of the shaft to a second portion of the shaft.

A related aspect pertains to an apparatus for performing a medical procedure, comprising: a shaft extending in a longitudinal direction and having a proximal end and a distal end, said shaft supporting an inflatable balloon; and a hub connected to the shaft by a spring or a threaded connection.

Still another aspect relates to a balloon catheter, comprising: an inflatable balloon; and a shaft extending in a longitudinal direction and having a proximal end and a distal end, the shaft including a first portion and a second portion adapted for constricting to move a portion of the balloon toward the proximal end when the balloon is inflated. The first portion may be connected to the second portion by a compression spring. The first portion may be connected to the second portion by a threaded engagement. The first portion may be adapted to telescope within the second portion.

Also disclosed is a method of using a catheter including a shaft to which a balloon is attached, comprising constricting the shaft on inflation of the balloon. The step of constricting may comprise telescoping first and second portions of the shaft. The constricting may be completed automatically or manually.

BRIEF DESCRIPTION OF THE FIGURES

FIGS. 10, 10a and 11 illustrate an angioplasty balloon according to a particular embodiment of the disclosure.

FIGS. 12 and 13 show a way in which the balloon of FIGS. 10, 10a and 11 is used.

MODES FOR CARRYING OUT THE INVENTION

The description provided below and in regard to the figures applies to all embodiments unless noted otherwise, and features common to each embodiment are similarly shown and numbered.

Figure 1:
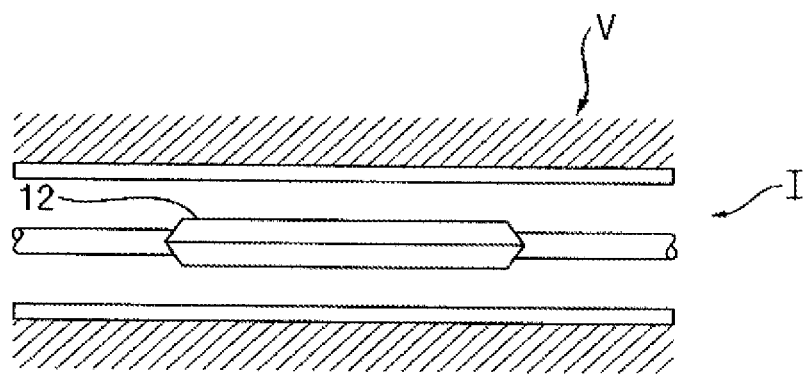
FIGS. 1 and 2 show the transition of an angioplasty balloon from a deflated, folded state to an expanded state within a vessel.
Figure 2:
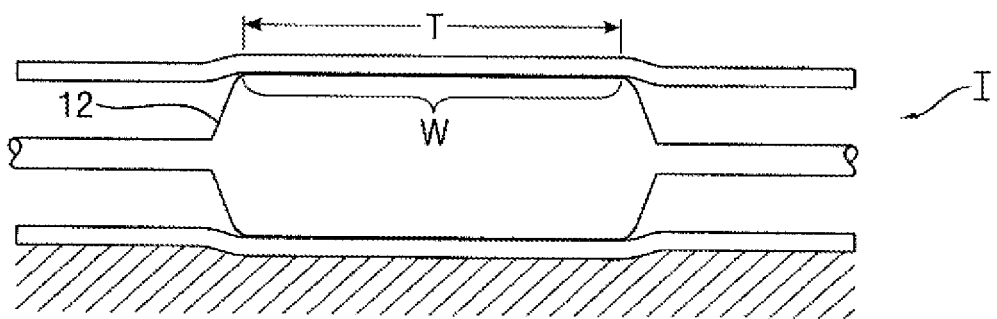
Figure 3:
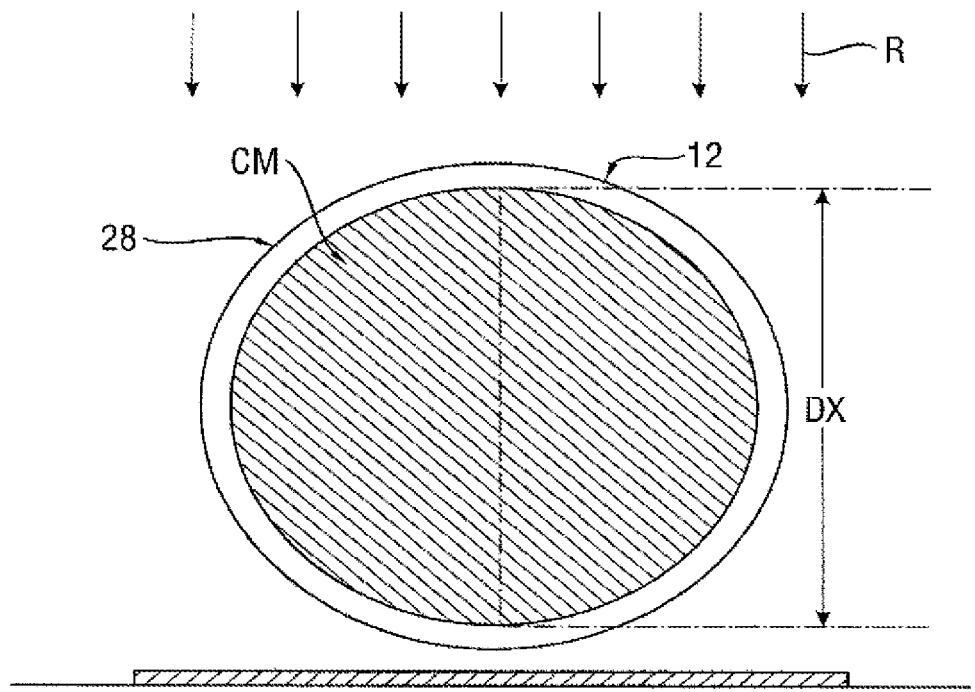
FIGS. 3 and 4 illustrate the visibility of an angioplasty balloon during an angioplasty procedure.
Figure 4:
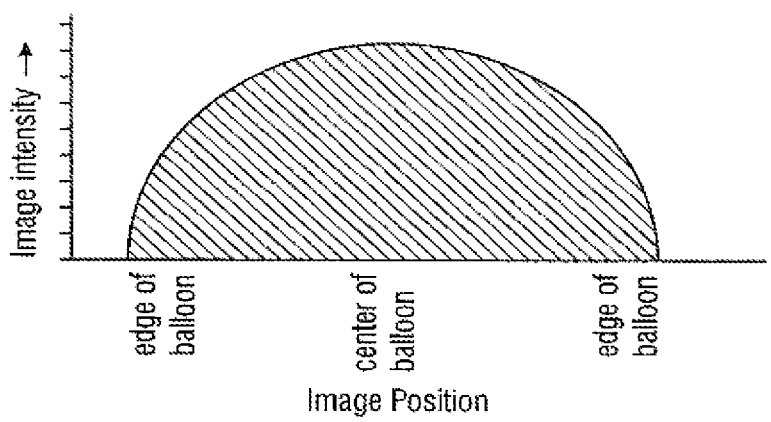
Figure 5:
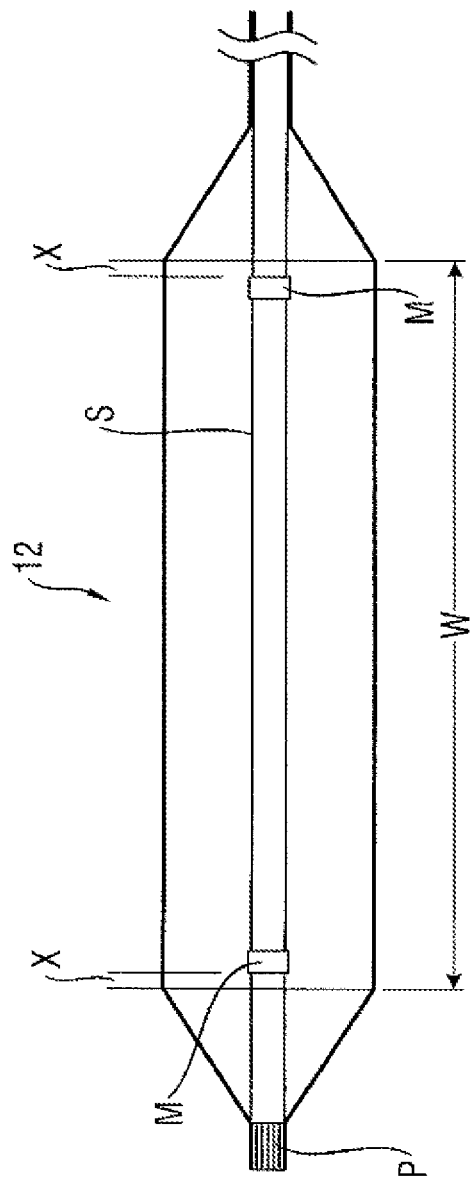
FIG. 5 illustrates the misalignment of a balloon within a vessel during an inflation of the balloon.
Figure 6:
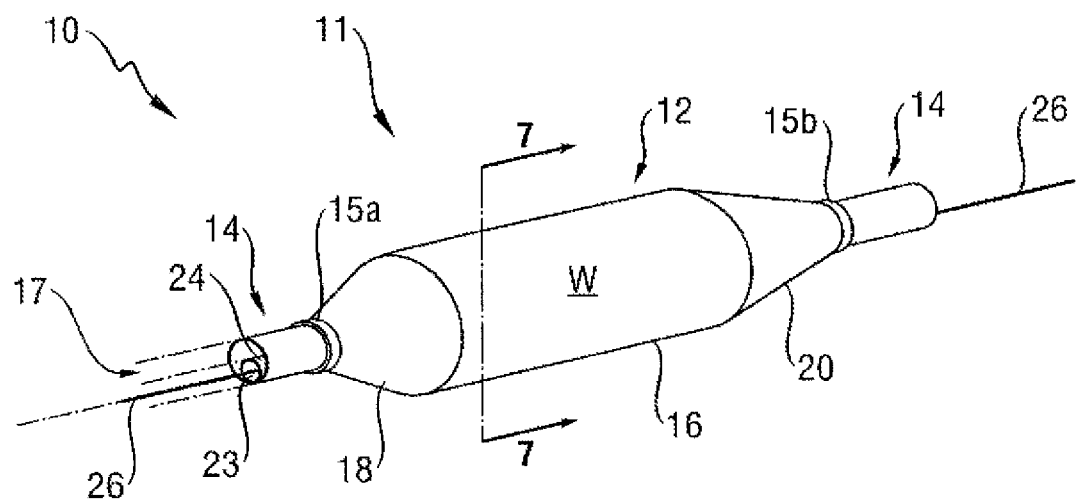
FIGS. 6, 7, 8 and 9 illustrate an angioplasty balloon according to an embodiment of the present disclosure.
Figure 7:
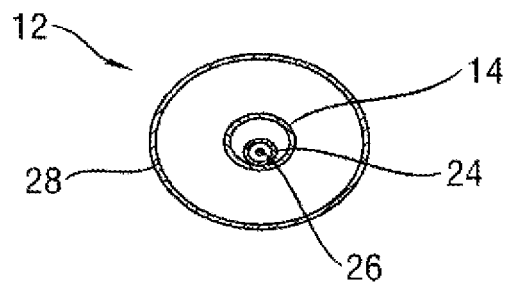
Figure 8:
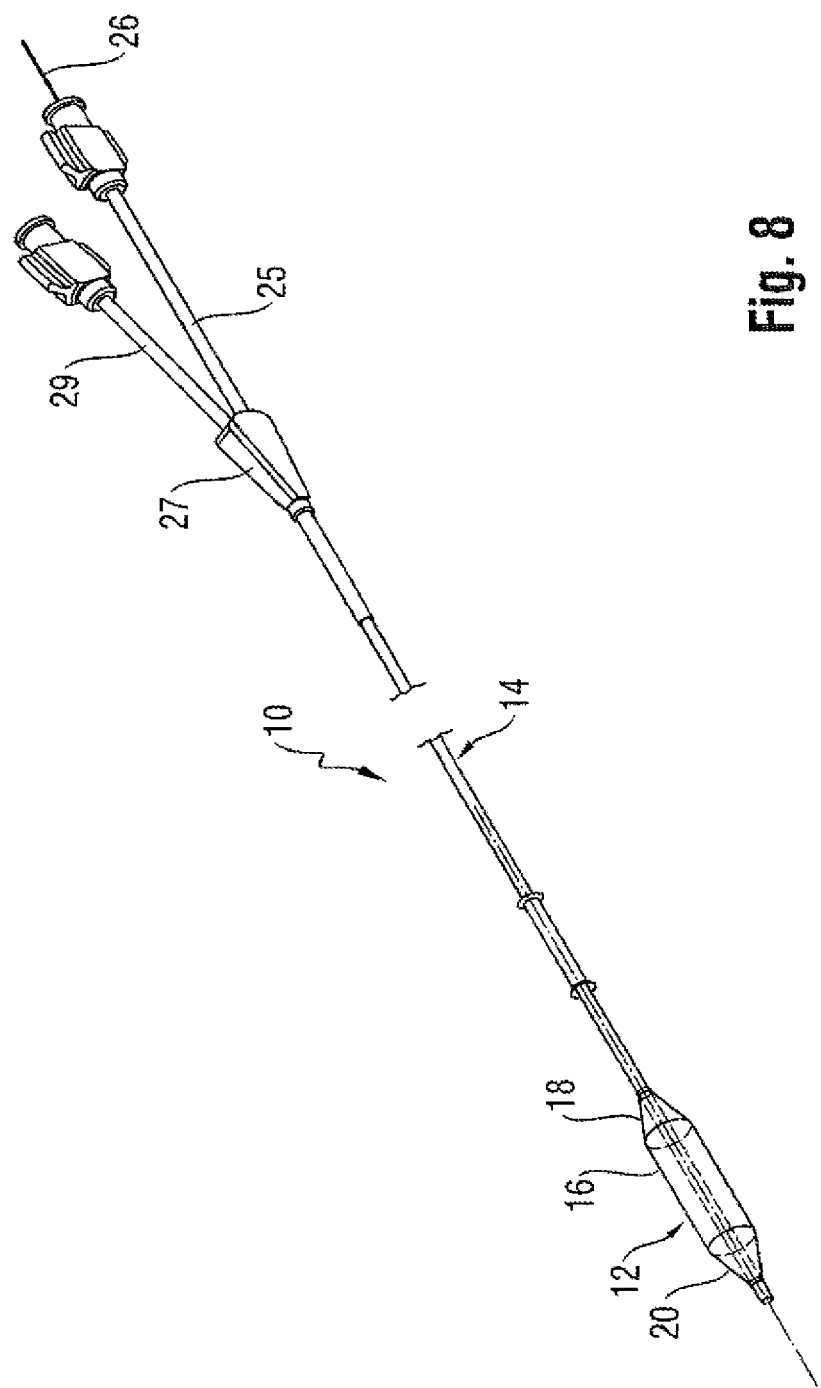

Provided is a catheter 10 having a distal portion 11 with a balloon 12 mounted on a catheter tube 14. Referring to FIGS. 6, 7, and 8, the balloon 12 has an intermediate section 16, or "barrel," and end sections 18, 20. In one embodiment, the end sections 18, 20 reduce in diameter to join the intermediate section 16 to the catheter tube 14 (and thus sections 18, 20 are generally termed cones or cone sections). The balloon 12 is sealed at balloon ends (proximal end 15a and distal end 15b) on the cone sections 18, 20 to allow the inflation of the balloon 12 via one or more inflation lumens 17 extending within catheter tube 14 and communicating with the interior of the balloon 12.

Figure 9:
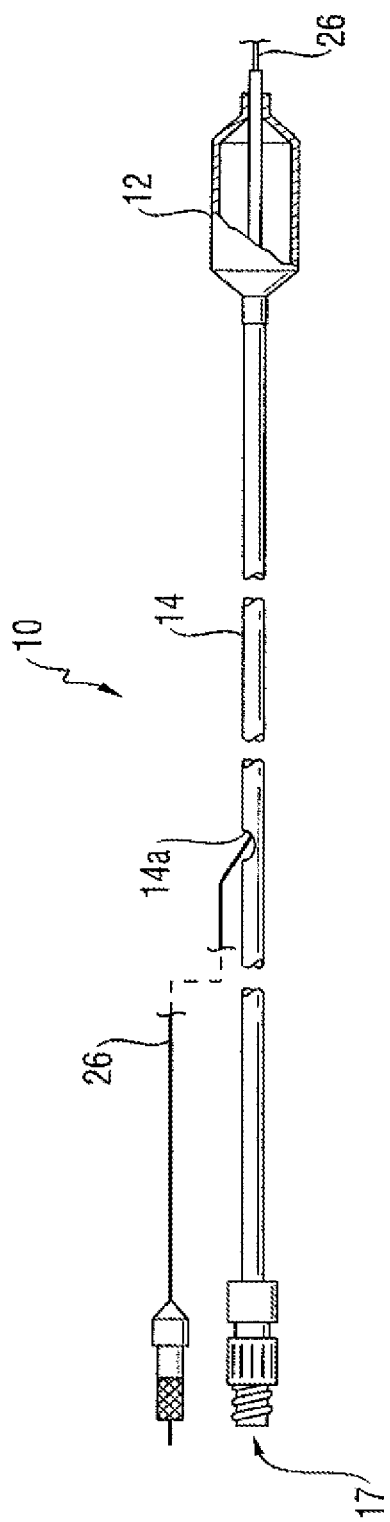

The catheter tube 14 also includes an elongated, tubular shaft 24 forming a guidewire lumen 23 that directs the guidewire 26 through the catheter 10, and along the distal end of which the balloon 12 may be located. As illustrated in FIG. 8, this guidewire 26 may extend through the proximal end of the catheter 10 and a first port 25 of a connector 27 into the lumen 23 to achieve an "over the wire" (OTW) arrangement, but could also be provided in a "rapid exchange" (RX) configuration, in which the guidewire 26 exits a lateral opening 14a closer to the distal end (see FIG. 9) or else is fed through the tip distally of the balloon 12 (not shown). A second port 29 may also be associated with catheter 10, such as by way of connector 27, for introducing a fluid (e.g., saline, a contrast agent, or both) into the interior compartment of the balloon 12 via the inflation lumen 17.

Balloon 12 may include a single or multi-layered balloon wall 28 forming the interior for receiving the inflation fluid. The balloon 12 may be a non-compliant balloon having a balloon wall 28 that maintains its size and shape in one or more directions when the balloon is inflated. The balloon 12 in such case also has a pre-determined surface area that remains constant during and after inflation, also has a pre-determined length and pre-determined diameter that each, or together, retrain constant during and after inflation.

However, the balloon 12 could be semi-compliant or compliant instead, depending on the particular use.

According to one aspect of the disclosure, the catheter 10 may be adapted for helping to allow the balloon 12 to foreshorten during inflation. This may be achieved by attaching a portion of the balloon 12 to the shaft 24 (part of which terms the inner member 24a within the balloon) in a manner that allows this portion of the balloon to move from closer to the distal end 15b to closer to the proximal end 15a when the balloon is inflated. In one embodiment, as shown in FIGS. 10 and 11, an actuator 30 includes a first portion 30a connected to the shaft 24 at a distal end portion thereof, and a second portion 30b adapted for receiving the first portion 30a, such as in a telescoping manner. The two portions 30a, 30b are wailingly engaged with each other so as to contain the inflation fluid within the balloon 12.

In use, and with combined reference to FIGS. 10 and 11 together, the balloon 12 is initially in a folded, deflated condition (12'), with the distal portion corresponding to end 15b extended in the distal direction (such as by the at least partial separation of the telescoping portions 30a, 30b). On inflation, the balloon 12 expands, and thus draws or urges the portions 30a, 30b to nest together and thus compact. This relative constriction or shortening of the shaft 24 prevents it from bowing under the resulting pressure that would exist if the balloon 12 was immovably fixed to the shaft, and thus helps to prevent the undesirable bowed condition and the corresponding misalignment that may result.

The portions 30a, 30b may also be connected together in a manner that limits movement in other directions besides the limited longitudinal movement. This may be achieved by providing one with a projection (such as a longitudinal rail) and the other with a corresponding recess (such as a matching longitudinal groove), as indicated by reference numeral 30c in FIG. 10a. More than one such mating arrangement may be provided. The arrangement may also include stoppers for defining the amount of relative movement permitted.

FIGS. 12 and 13 illustrate that the actuator 30 may also be provided at the proximal end 15a of the balloon 12. As the skilled person can infer from those figures, the actuator is the same as that shown in FIGS. 10, 10a and 11. In FIG. 12, the balloon 12 is in the uninflated state (12') and, thus, the portions 30a, 30b are expanded. When inflated the portions 30a, 30b nest to provide the desired foreshortening of the shaft 24. In this embodiment, the shaft 24 is shown as being a "dual lumen" approach, with an inflation lumen 17 and a guidewire lumen 23 (in communication with an inflation opening O in the shaft 24 inside the balloon 12) separated by a divider.

Figure 14:
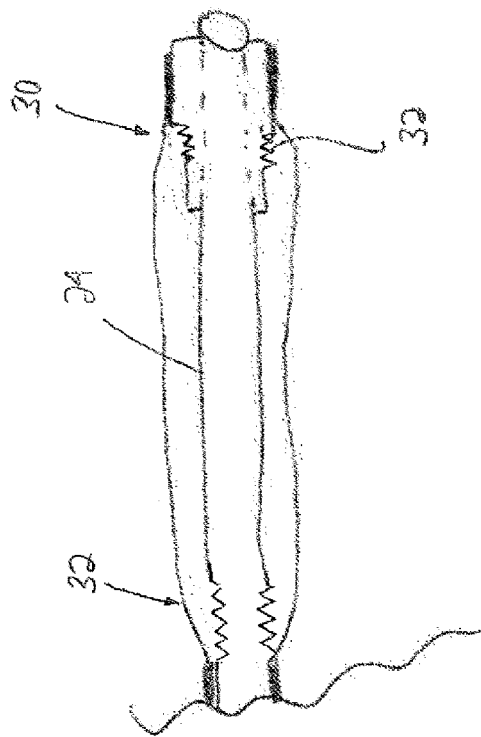
FIGS. 14 and 15 show a further embodiment of the disclosure.
Figure 15:
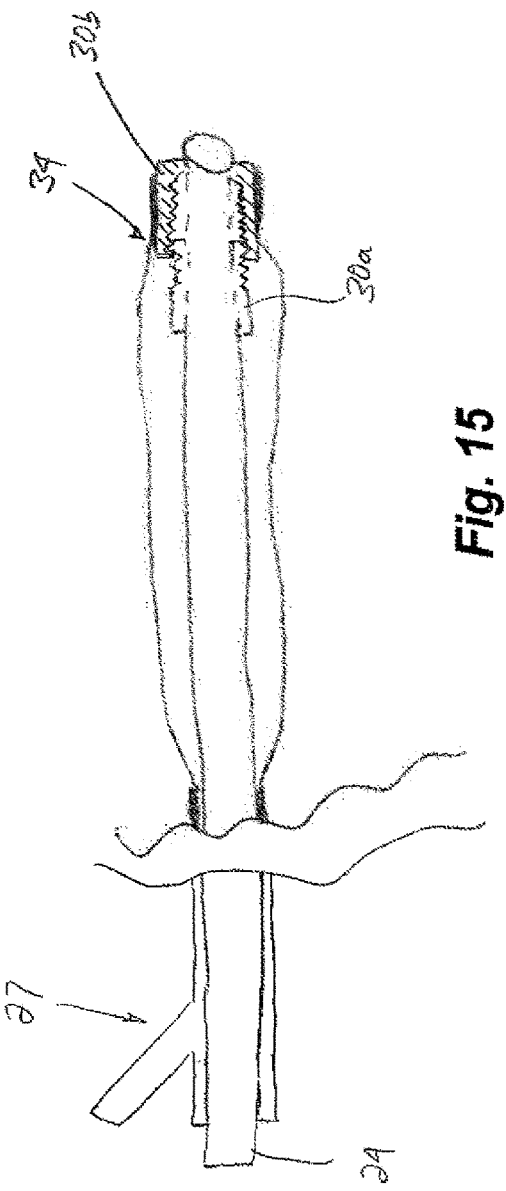

Turning to FIG. 14, an actuator 30 in the form of a biasing element, or spring 32 may also be provided for urging one portion 30a, 30b or the other in either the proximal direction or the distal direction depending on the inflation condition. As is clear from FIG. 14, the biasing element 32 is arranged so as to shorten the shaft 24 when the balloon 12 is inflated. In lieu of the portions 30a, 30b, one or more springs 32 may also be provided in an independent manner along another part of the shaft 24, as shown in FIG. 15. In both instances, the spring 32 may comprise a compression spring that is normally expanded and then compresses and shortens the shaft 24, either as a result of inflation in an automatic manner, or as a result of a manual adjustment, as discussed below. While illustrated together, it should be appreciated that only one of these arrangements could be used, or each could be used a plurality of times.

Figure 16:
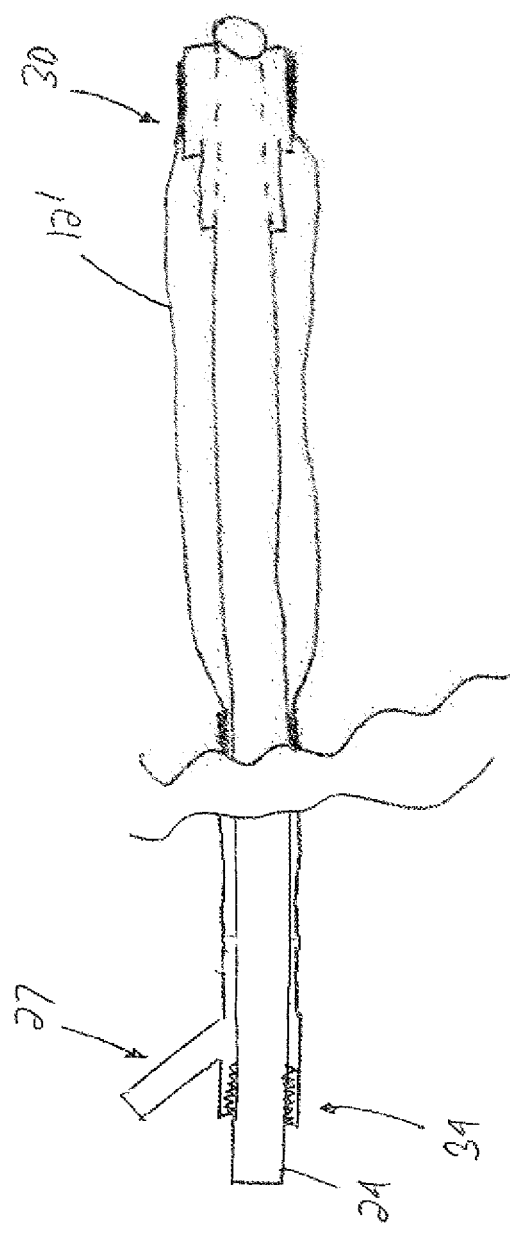
FIGS. 16 and 17 show yet another embodiment of the disclosure.
Figure 17:
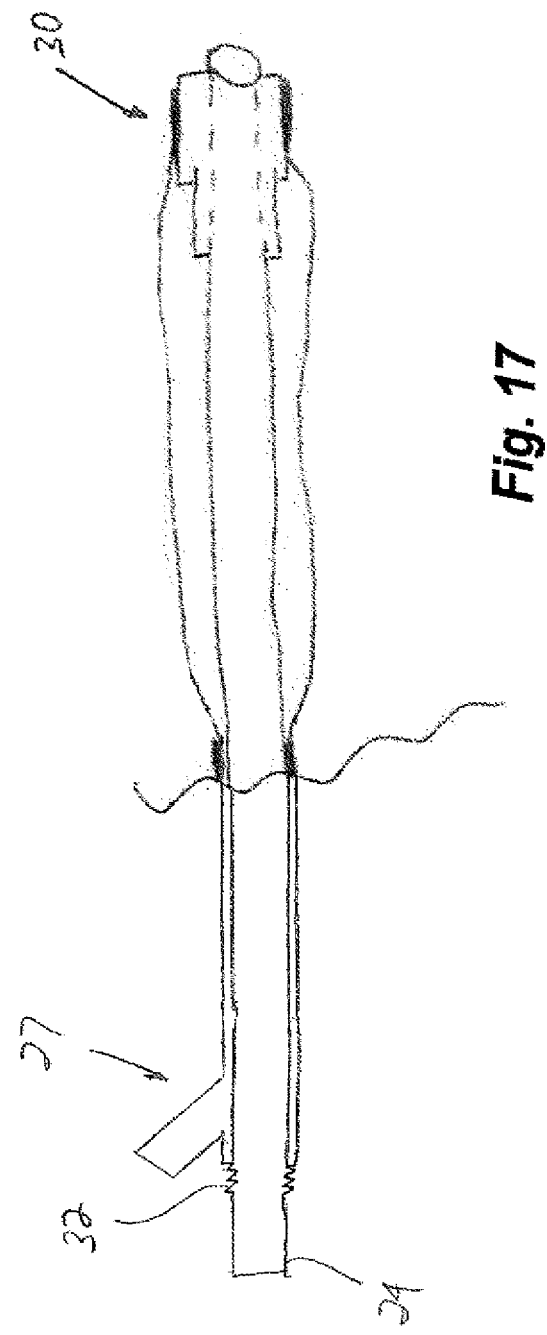

The portions 30a, 30b, may also engage each other using means such as a threaded connection 34 (FIG. 15), which may allow for manual adjustments to be made to the relative movement. This may be achieved by providing an inner shaft 24 that may be rotated, such as by grasping at the proximal end of the catheter 10 at a connector 27 or hub. Thus, by rotating the inner shaft 24 during inflation, it may be manually foreshortened. The threaded connection 34 may also be provided between the connector 27 or hub and a proximal portion of the shaft 24, as shown in FIG. 16, and the same is the case for the spring 32, as shown in FIG. 17 (which in this placement may be a tension or a compression spring). As is evident to the skilled person from FIG. 17, the hub 27 is preferably connected to a proximal end of the balloon such that by way of the connector, the balloon can be inflated. The connection could also be made by way of a rail connecting the two structures, possibly with the creation of friction (such as by providing pads) to allow for control of the relative movement. Combinations of any of these approaches with those shown in FIGS. 12-17 may also be utilized.

While the disclosure presents certain embodiments to illustrate the inventive concepts, numerous modifications, alterations, and changes to the described embodiments are possible without departing from the sphere and scope of the present invention, as defined in the appended claims. For example, the ranges and numerical values provided in the various embodiments are subject to variation due to tolerances, due to variations in environmental factors and material quality, and due to modifications of the structure and shape of the balloon, and thus can be considered to be approximate and the terms "approximately" or "substantially" means that the relevant value can, at minimum, vary because of such factors. Accordingly, it is intended that the present disclosure not be limited to the described embodiments, but that it has the full scope defined by the language of the following claims, and equivalents thereof.

The invention claimed is:

1. A balloon catheter for use in connection with a guidewire, comprising:
    a catheter shaft extending in a longitudinal direction and having a proximal end and a distal end, the catheter shaft including an inflation lumen and a guidewire lumen for receiving the guidewire; and
    an inflatable balloon including a distal end portion positioned along the catheter shaft, the balloon having at least one portion connected to the proximal or distal end of the catheter shaft by an actuator and adapted for moving toward the proximal or distal end thereof on inflation of the balloon to expand from a deflated condition while the distal end of the catheter shaft remains connected to the balloon;
    wherein the inflation lumen is capable of delivering inflation fluid to inflate the balloon while the catheter shaft is sealed to the inflatable balloon;
    wherein the actuator comprises a first portion attached to the inflatable balloon and a second portion attached directly to the catheter shaft within the inflatable balloon and movable independent of the first portion; and
    wherein the first portion of the actuator is connected to a proximal portion of the balloon.

2. The catheter of claim 1, wherein the actuator further comprises a spring, the spring being arranged so as to compress when the inflatable balloon is inflated.

3. The catheter of claim 1, further including a hub connected to the proximal end of the shaft in a manner that permits relative movement between the hub and the shaft in a longitudinal direction.

4. The catheter of claim 3, wherein the hub is connected to the shaft by a spring.

5. The catheter of claim 3, wherein the hub is connected to the shaft by a threaded engagement.

6. The catheter of claim 1, wherein the shaft constricts and shortens in a longitudinal direction on inflation of the inflatable balloon.

7. The catheter of claim 1, wherein the shaft includes at least one compression spring.

8. The catheter of claim 1, wherein the distal end portion of the inflatable balloon is attached via the actuator to an inner tube forming the guidewire lumen, and a proximal end portion of the balloon is attached to an outer tube at least partially surrounding the inner tube.

9. The catheter of claim 1, wherein the shaft extends continuously from a proximal end portion of the inflatable balloon through the distal end portion of the inflatable balloon to an open end, said actuator comprising a telescoping connector.

10. A balloon catheter for use with a guidewire, comprising:
   a catheter shaft having a proximal end, a distal end, a guidewire lumen for receiving the guidewire, and an inflation lumen;
   an inflatable balloon extending along the catheter shaft from a proximal end portion of the balloon to a distal end portion of the balloon; and
   a connector having a first portion attached to the inflatable balloon and a second portion for receiving the catheter shaft, the first portion adapted for sliding along the second portion to allow the inflatable balloon distal end portion to move toward the proximal end of the catheter shaft on inflation of the inflatable balloon to expand to an inflated condition from a deflated condition while the distal end of the catheter shaft remains connected to the inflatable balloon and the first and second portions remain sealingly engaged so as to contain the inflation fluid within the inflatable balloon;
   wherein the first portion of the connector is attached to the proximal end portion of the inflatable balloon.

11. The catheter of claim 10, wherein a portion of the catheter shaft proximal to the connector has a first diameter, the first portion of the connector has a second diameter greater than the first diameter, and the second portion of the connector has a third diameter greater than the second diameter.

12. The apparatus of claim 10, wherein the catheter shaft extends into a hub.

13. The apparatus of claim 10, wherein the connector is located at a proximal end of the inflatable balloon.

14. A balloon catheter for use in connection with a guidewire, comprising:
   a catheter shaft extending in a longitudinal direction and having a proximal end and a distal end, the catheter shaft including an inflation lumen and a guidewire lumen for receiving the guidewire; and
   an inflatable balloon including a distal end portion positioned along the catheter shaft, the balloon having at least one portion connected to the proximal or distal end of the catheter shaft by an actuator external to the catheter shaft and adapted for moving toward the proximal or distal end thereof on inflation of the inflatable balloon to expand from a deflated condition while the distal end of the catheter shaft remains connected to the inflatable balloon;
   wherein the inflation lumen is capable of delivering inflation fluid to inflate the balloon while the catheter shaft is sealed to the inflatable balloon;
   wherein the actuator comprises a first portion attached to the inflatable balloon and a second portion attached directly to the catheter shaft within the inflatable balloon and attached to the first portion so as to be movable independent of the first portion; and
   wherein the first portion of the actuator is attached to a proximal portion of the inflatable balloon.

* * * * *